United States Patent [19]
Bell et al.

[11] Patent Number: 5,981,560
[45] Date of Patent: *Nov. 9, 1999

[54] TRIAZOLE ANTIFUNGAL AGENTS

[75] Inventors: Andrew Simon Bell; Peter Thomas Stephenson, both of Sandwich, United Kingdom

[73] Assignee: Pfizer Inc., New York, N.Y.

[ * ] Notice: This patent issued on a continued prosecution application filed under 37 CFR 1.53(d), and is subject to the twenty year patent term provisions of 35 U.S.C. 154(a)(2).

[21] Appl. No.: 08/828,754

[22] Filed: Mar. 18, 1997

[30] Foreign Application Priority Data

Mar. 19, 1996 [GB] United Kingdom ............... 9605705

[51] Int. Cl.$^6$ .............. A61K 31/41; C07D 403/10; C07D 249/08
[52] U.S. Cl. .............. 514/383; 548/266.6; 548/267.6; 548/267.8; 548/268.6
[58] Field of Search .............. 514/383; 548/266.6, 548/267.6, 267.8, 268.6

[56] References Cited

U.S. PATENT DOCUMENTS 5,629,332  5/1997  Kodama et al. .................. 514/383

Primary Examiner—Patricia L. Morris
Attorney, Agent, or Firm—Peter C. Richardson; Paul H. Ginsburg; Jolene W. Appleman

[57] ABSTRACT

An antifungal compound of formula (I):

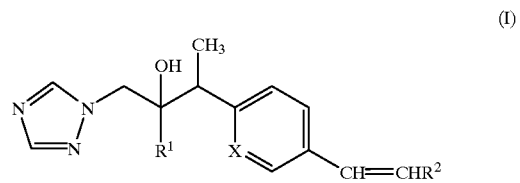

or a pharmaceutically acceptable salt thereof, or a pharmaceutically acceptable solvate of either entity, wherein X is CH or N; $R^1$ is phenyl substituted with 1 to 3 substituents each independently selected from halo and $CF_3$; $R^2$ is (hydroxy)$C_1$–$C_4$ alkyl, $CONH_2$, $S(O)_m(C_1$–$C_4$ alkyl), Ar or Het; m is 1 or 2; Ar is phenyl optionally monosubstituted with halo or $CF_3$; and Het is a C-linked 6-membered nitrogen-containing aromatic heterocyclic group containing 1 or 2 nitrogen atoms, or a C- or N-linked 5-membered nitrogen-containing aromatic heterocyclic group containing from 2 to 4 nitrogen atoms, wherein either of said heterocyclic groups is optionally substituted with $C_1$–$C_4$ alkyl or ($C_1$–$C_4$ alkoxy)methyl.

7 Claims, No Drawings

TRIAZOLE ANTIFUNGAL AGENTS

This invention relates to triazole derivatives which have antifungal activity and are useful in the treatment of fungal infections in animals, including human beings.

Thus the invention provides compounds of formula (I):

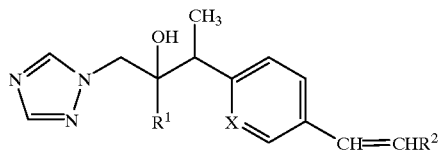

(I)

pharmaceutically acceptable salts thereof, and pharmaceutically acceptable solvates of either entity, wherein X is CH or N;

$R^1$ is phenyl substituted with 1 to 3 substituents each independently selected from halo and $CF_3$;

$R^2$ is (hydroxy)$C_1$–$C_4$ alkyd $CONH_2$, $S(O)_m(C_1–C_4$ alkyl), Ar or Het;

m is 1 or 2;

Ar is phenyl optionally monosubstituted with halo or $CF_3$;

and Het is a C-linked 6-membered nitrogen-containing aromatic heterocyclic group containing 1 or 2 nitrogen atoms, or a C- or N-linked 5-membered nitrogen-containing aromatic heterocyclic group containing from 2 to 4 nitrogen atoms, wherein either of said heterocyclic groups is optionally substituted with $C_1$–$C_4$ alkyl or ($C_1$–$C_4$ alkoxy)methyl.

In the above definition, unless otherwise indicated, alkyl and alkoxy groups having three or more carbon atoms may be straight or branched chain; halo means fluoro, chloro, bromo or iodo. In addition. Het is selected from pyridyl, pyridazinyl, pyrimidinyl, pyrazinyl, pyrazolyl, imidazolyl, triazolyl or tetrazolyl.

The compounds of formula (I) contain at least two chiral centres and therefore can exist as stereoisomers, i.e. as enantiomers or diastereoisomers, as well as mixtures thereof. The invention includes both the individual stereoisomers of the compounds of formula (I) together with mixtures thereof. Separation of diastereoisomers may be achieved by conventional techniques, e.g. by fractional crystallisation or chromatography (including HPLC) of a diastereoisomeric mixture of a compound of formula (I) or a suitable salt or derivative thereof. An individual enantiomer of a compound of formula (I) may also be prepared from a corresponding optically pure intermediate or by resolution, either by HPLC of the racemate using a suitable chiral support or by fractional crystallisation of the diastereoisomeric salts formed by reaction of the racemate with a suitable optically active acid.

The preferred stereoisomers of formula (I) have the (2R,3S)-configuration of formula (IA):

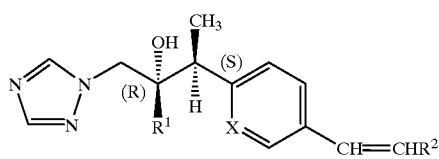

(IA)

Furthermore, the compounds of formula (I) may exist as cis- or trans-alkene isomers and the invention also includes both separate individual isomers and mixtures thereof. The preferred isomers are the trans-isomers.

Certain compound of formula (I) may also exist in tautomeric forms and the invention includes both separate individual tautomers and mixtures thereof.

Also included in the invention are radiolabelled derivatives of compounds of formula (I) which are suitable for biological studies.

The pharmaceutically acceptable salts of the compounds of formula (I) are, for example, non-toxic acid addition salts formed with inorganic acids such as hydrochloric, hydrobromic, sulphuric and phosphoric acid, with organocarboxylic acids, or with organo-sulphonic acids. Certain compounds of formula (I) can also provide pharmaceutically acceptable metal salts, in particular non-toxic alkali metal salts, with bases. Examples include the sodium and potassium salts. For a review of suitable pharmaceutical salts, see J. Pharm. Sci., 1977, 66, 1.

A preferred group of compounds of formula (I) is that wherein $R^1$ is phenyl substituted by 1 or 2 substituents each independently selected from F and Cl; $R^2$ is hydroxypropyl, $CONH_2$, $SO_2CH_3$, Ar or Het; Ar is fluorophenyl; Het is a pyridyl, pyrazolyl, imidazolyl or triazolyl group, wherein said pyrazolyl group is substituted with methyl and said triazolyl group is optionally substituted with ethoxymethyl; and X is as previously defined for formula (I).

A more preferred group of compounds of formula (I) is that wherein $R^1$ is 2,4-difluorophenyl; $R^2$ is $C(CH_3)_2OH$, $CONH_2$, $SO_2CH_3$, 4-fluorophenyl, 2-pyridyl, 1-methylpyrazol-5-yl, imidazol-1-yl, 1,2,3-triazol-4-yl or 1-ethoxymethyl-1,2,3-triazol-5-yl; and X is as previously defined for formula (I).

Particularly preferred compounds of the invention include:

trans-(2R,3S)-1-(1,2,4-triazol-1-yl)-2-(2,4-difluorophenyl)-3-{4-[2-(1-methylpyrazol-5-yl)ethenyl]phenyl}butan-2-ol;

trans-(2R,3S/2S,3R)-1-(1,2,4-triazol-1-yl)-2-(2,4-difluorophenyl)-3-{4-[2-(imidazol-1-yl)ethenyl]phenyl}butan-2-ol; and trans-(2R,3S/2S,3R)-1-(1,2,4-triazol-1-yl)-2-(2,4-difluorophenyl)-3-[5-(2-carbamoylethenyl)pyrid-2-yl]butan-2-ol;

and pharmaceutically acceptable salts thereof, and pharmaceutically acceptable solvates of either entity.

In another aspect, the present invention provides processes for the preparation of compounds of formula (I), their pharmaceutically acceptable salts, and pharmaceutically acceptable solvates of either entity.

A compound of formula (I) may be prepared from a compound of formula (II):

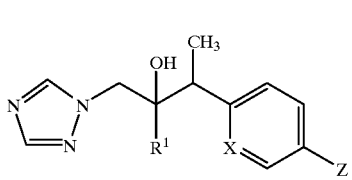

(II)

wherein Z is bromo or iodo, and X and $R^1$ are as previously defined for formula (I), by treatment with a compound of formula (III):

$CH_2=CHR^2$  (III)

wherein $R^2$ is as previously defined for formula (I), under typical Heck reaction conditions. The reaction is generally carried out using from about a 20 to about a 100% excess of the required alkene and from about a 50 to about a 100% excess of a tertiary amine, in the presence of from about 0.05 to about 0.60 equivalent of a palladium salt and from about 0.10 to about 1.10 equivalents of a tertiary arylphosphine, in a suitable solvent such as acetonitrile or dimethylformamide, at from about 80 to about 160° C. Preferably the tertiary amine is triethylamine, the palladium salt is palladium acetate, the phosphine is either tri-o-tolylphosphine or 1,1'-bis(diphenylphosphino)ferrocene, and the reaction is conducted in refluxing acetonitrile.

A compound of formula (II) may be prepared by a variety of synthetic procedures. For example one such procedure, which is preferred when X is N, involves the reaction of a compound of formula (IV):

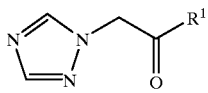

(IV)

wherein $R^1$ is as previously defined for formula (II), with an organometallic compound of formula (V):

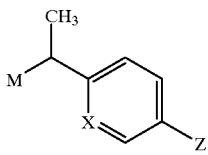

(V)

wherein M is a suitable metal (e.g. lithium, sodium or potassium) or metal halide (e.g. magnesium halide or zinc halide), and X and Z are as previously defined for formula (II).

An organometallic compound of formula (V) wherein M is a suitable metal is preferably generated in situ by deprotonation of the corresponding alkane precursor (i.e. a compound of formula (V) wherein M is hydrogen) with a suitable base, e.g. lithium or potassium diisopropylamide or lithium, sodium or potassium bis(trimethylsilyl)amide.

An organometallic compound of formula (V) wherein M is a suitable metal halide, e.g. a Grignard reagent or organozincate, can be prepared either by treatment in situ of the corresponding organometallic compound of formula (V) wherein M is lithium with a suitable metal halide, e.g. magnesium bromide or zinc iodide, or by treatment of the corresponding alkyl halide precursor (i.e. a compound of formula (V) wherein M is chloro, bromo or iodo) with magnesium or zinc respectively, optionally using iodine to promote the reaction.

Preferably (V) wherein M is chloro, bromo or iodo is converted to the corresponding zincate in the presence of (IV) in a suitable solvent at about room temperature in an inert atmosphere by treating it with zinc in the presence of iodine. This may be achieved in tetrahydrofuran as solvent using about 2.6 equivalents of zinc powder, followed by 0.2 equivalent of iodine, which leads to an exothermic reaction.

The compounds of formula (IV) are either known, e.g. see EP-A-044605, EP-A-069442 or GB-A-1464224, or may be prepared by methods similar to those described therein.

An alternative synthetic procedure for preparing a compound of formula (II), which is preferred when X is CH, involves the reduction of a compound of formula (VI):

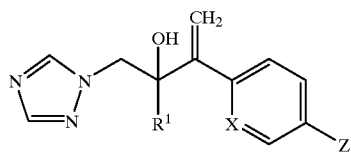

(VI)

herein Z, X and $R^1$ are as previously defined for formula (II).

The reduction is conveniently effected using diimide generated in situ. Thus diimide precursor, such as p-toluenesulphonylhydrazide, and (VI) are combined in a suitable solvent, e.g. toluene, and the reaction conducted at the reflux temperature of the reaction medium.

The reduction may also be carried out by catalytic hydrogenation using a suitable catalyst such as palladium on charcoal in an appropriate solvent, e.g. a $C_1$–$C_3$ alkanol.

A compound of formula (VI) may be prepared by reaction of an epoxide of formula (VII):

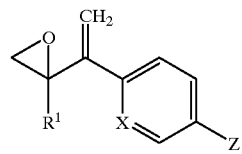

(VII)

wherein Z, X and $R^1$ are as previously defined for formula (VI), with 1,2,4-triazole in the presence of a base or with a tetraalkylammonium or alkali metal salt (preferably the sodium salt) of 1,2,4-triazole in a suitable solvent such as dimethylformamide, methanol or aqueous acetone. The reaction is conveniently carried out using about a 50% excess of the said sodium salt in dry dimethylformamide at about 70° C.

The resulting racemic mixture of 2R and 2S enantiomers may be conveniently resolved at this stage, e.g. by chromatography using a chiral stationary phase, and the 2R enantiomer reduced as above to afford, after further chromatographic resolution, the preferred 2R, 3S enantiomer of a compound of formula (II).

A compound of formula (VII) may be prepared by methylenation of a ketone of formula (VIII):

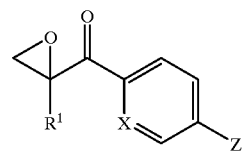

(VIII)

wherein Z, X and $R^1$ are as previously defined for formula (VII), under standard Wittig or Wittig-Horner reaction conditions. For example, (VIII) is treated with about a 30% excess of the ylid generated in situ from methyltriphenylphosphonium bromide and a strong base, e.g. n-butyllithium in hexane solution, in a suitable solvent such as dry tetrahydrofuran at from about −20° C. to about room temperature in an inert atmosphere.

A compound of formula (VIII) may be prepared by epoxidation of an alkene of formula (IX):

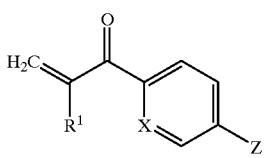

(IX)

wherein Z, X and R$^1$ are as previously defined for formula (VIII).

Of the plethora of oxidation reagents and reactions available, a convenient technique is the use of phase transfer catalysis using, for example, a quatenary ammonium salt as catalyst. Typical conditions are to employ about a 10% excess of an oxidant such as t-butyl hydroperoxide in a suitable solvent, e.g. toluene, in the presence of about 0.1 equivalent of benzyltrimethylammonium hydroxide in aqueous solution at about room temperature.

A compound of formula (IX) may be prepared by methylenation of a compound of formula (X):

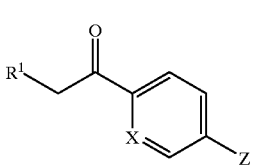

(X)

wherein Z, X and R$^1$ are as previously defined for formula (IX), using a Mannich-type reaction. This may be conveniently achieved by treating (X) in the presence of about a 5-fold excess of acetic anhydride with about a 50% excess of bis(dimethylamino)methane at about room temperature.

A compound of formula (X) may be prepared by any of a myriad of standard α-methyleneketone syntheses. For example, a substituted benzyl halide of formula (XI):

 (XI)

wherein Y is chloro, bromo or iodo and R$^1$ is as previously defined for formula (X), is converted to the corresponding Grignard reagent which is then reacted with about a 40% excess of a hydroxamic acid derivative of formula (XII):

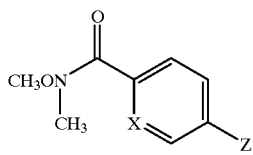

(XII)

wherein Z and X are as previously defined for formula (X), in a suitable solvent such as dry ether at from about −70° C. to about room temperature in an inert atmosphere.

Certain compounds of formula (I) wherein R$^2$ is a C-linked 5-membered nitrogen-containing aromatic heterocyclic group containing from 2 to 4 nitrogen atoms substituted on a nitrogen atom with C$_1$–C$_4$ alkyl or (C$_1$–C$_4$ alkoxy)methyl can be prepared by N-alkylation of the corresponding unsubstituted compounds, e.g. by using the appropriate C$_1$–C$_4$ alkyl halide or (C$_1$–C$_4$ alkoxy)methyl halide (e.g. chloride or bromide), typically in the presence of an acid acceptor in a suitable solvent. When tautomerism of the ring is possible, alkylation may occur on one or more nitrogen atoms but the resulting mixture of products can be separated by chromatograpy.

Alternatively, the reverse transformation may be exploited. For example, a compound of formula (I) bearing a N-(C$_1$–C$_4$ alkoxy)methyl substituent within R$^2$ may be converted to the corresponding unsubstituted derivative by acid hydrolysis in a suitable solvent. The reaction can be conveniently carried out using dilute hydrochloric acid in aqueous ethanol as solvent at the reflux temperature of the reaction medium.

A compound of formula (III) may be prepared by methylenation of the corresponding aldehyde (R$^2$CH=O) by Wittig or Wittig-Horner methodology as described for the conversion of (VIII) to (VII). Where necessary, the required aldehydes are obtained by formylation, e.g. using dimethylformamide, of the corresponding (hetero) aryllithium under standard reaction conditions.

The intermediate alkane and alkyl halide precursors of (V) and intermediates of formulae (III), (XI) and (XII), when neither commercially available nor subsequently described, can be obtained either by analogy with the processes described in the Preparations section or by conventional synthetic procedures, in accordance with standard textbooks on organic chemistry or literature precedent, from readily accessible starting materials using appropriate reagents and reaction conditions.

Moreover, persons skilled in the art will be aware of variations of, and alternatives to, those processes described hereinafter in the Examples and Preparations sections which allow the compounds defined by formula (I) to be obtained.

The pharmaceutically acceptable acid addition salts of the compounds of formula (I) may also be prepared in a conventional manner. For example a solution of the free base is treated with the appropriate acid, either neat or in a suitable solvent, and the resulting salt isolated either by filtration or by evaporation under reduced pressure of the reaction solvent. Pharmaceutically acceptable base addition salts can be obtained in an analogous manner by treating a solution of a compound of formula (I) with the appropriate base. Both types of salt may be formed or interconverted using ion-exchange resin techniques.

The compounds of formula (I), their pharmaceutically acceptable salts, and pharmaceutically acceptable solvates of either entity are antifungal agents, useful in the curative or prophylactic treatment of fungal infections in animals, including human beings. For example, they are useful in treating superficial fungal infections in humans caused by, among other organisms, species of Candida, Trichophyton, Microsporum or Epidermophyton, or in mucosal infections caused by *Candida albicans* (e.g. thrush and vaginal candidiasis) and they can also be used in the treatment of systemic fungal infections caused by, for example, species of Candida (e.g. *Candida albicans*), *Cryptococcus neoformans*, *Aspergillus flavus*, *Aspergillus fumigatus*, Coccidioides, Paracoccidioides, Histoplasma or Blastomyces. Indeed, they possess potent, broad spectrum antifungal activity both in vitro and in vivo.

Certain compounds of the invention have been found to have unexpectedly good broad spectrum activity, including excellent activity against the clinically important Aspergillus spp. fungi.

The in vitro evaluation of the antifungal activity of the compounds can be performed by determining the minimum inhibitory concentration (m.i.c.), which is the concentration of a test compound, in a suitable medium, at which growth of the particular micro-organism fails to occur. In practice, a series of agar plates, or liquid medium in microtiter plates, each having the test compound incorporated at a particular concentration, is inoculated with a standard culture of, for example, *Cryptococcus neoformans*, and each plate is then incubated for 48 hours at 37° C. The plates are then examined for the presence or absence of growth of the fungus and the appropriate m.i.c. value is noted. Other micro-organisms used in such tests can include *Candida albicans, Asperaillus fumigatus,* Trichophyton spp., Microsporum spp., *Epidermophyton floccosum, Coccidioides immitis* and *Torulopsis glabrata*.

The in vivo evaluation of the compounds can be carried out at a series of dose levels by intraperitoneal or intravenous injection, or by oral administration, to mice or rats which are inoculated with, e.g. a strain of *Candida albicans, Aspergillus fumigatus* or *Cryptococcus neoformans*. Activity may be based on the number of survivors from a treated group of mice after the death of an untreated group of mice.

For Candida spp. infection models the dose level at which the compound provides 50% protection against the lethal effect of the infection ($PD_{50}$) is also assessed.

For Aspergillus spp. infection models the number of mice cured of the infection after a set dose allows further assessment of activity.

For Cryptococcus spp. infection models the number of colony forming units existing after a set dose is assessed and compared with control to determine compound efficacy. A preliminary assessment of potential liver toxicity may also be made on the basis of increase in liver weight relative to control.

For human use, the antifungal compounds of the invention can be administered alone, but will generally be administered in admixture with a pharmaceutical carrier selected with regard to the intended route of administration and standard pharmaceutical practice. For example, they can be administered orally in the form of tablets containing such excipients as starch or lactose, or in capsules or ovules either alone or in admixture with excipients, or in the form of elixirs, solutions or suspensions containing flavouring or colouring agents. They can be injected parenterally, for example intravenously, intramuscularly or subcutaneously. For parenteral administration, they are best used in the form of a sterile aqueous solution which may contain other substances, for example enough salts or glucose to make the solution isotonic with blood.

The solubility of a compound of formula (I) in an aqueous medium may be improved by complexation with a hydroxyalkyl (see EP-A-0149197) or sulfoalkyl (see WO 91/11172) derivative of a cyclodextrin in the preparation of an appropriate pharmaceutical composition. Preferably the cyclodextrin used is alpha-, beta- or gamma-cyclodextrin.

For oral and parenteral administration to human patients, the daily dosage level of the antifungal compounds of the invention will be from 0.01 to 20 mg/kg (in single or divided doses). Thus tablets or capsules of the compounds will contain from 5 mg to 0.5 g of active compound for administration singly, or two or more at a time, as appropriate. The physician in any event will determine the actual dosage which will be most suitable for an individual patient and it will vary with the age, weight and response of the particular patient. The above dosages are exemplary of the average case; there can, of course, be instances where higher or lower dosage ranges are merited and such are within the scope of this invention.

Alternatively, the antifungal compounds of the invention can be administered in the form of a suppository or pessary, or they may be applied topically in the form of a lotion, solution, cream, ointment or dusting powder. For example, they can be incorporated into a cream consisting of an aqueous emulsion of polyethylene glycols or liquid paraffin, or they can be incorporated, at a concentration of from 1 to 10%, into an ointment consisting of a white wax or white soft paraffin base together with such stabilisers and preservatives as may be required.

Thus the invention provides a pharmaceutical composition comprising a compound of formula (I), or a pharmaceutically acceptable salt thereof, or a pharmaceutically acceptable solvate of either entity, together with a pharmaceutically acceptable diluent or carrier.

The invention also provides a compound of formula (I), or a pharmaceutically acceptable salt thereof, or a pharmaceutically acceptable solvate of either entity, or a pharmaceutical composition containing any of the foregoing, for use as a medicament.

The invention further includes the use of a compound of formula (I), or a pharmaceutically acceptable salt thereof, or a pharmaceutically acceptable solvate of either entity, or a pharmaceutical composition containing any of the foregoing, for the manufacture of a medicament for the curative or prophylactic treatment of fungal infections.

In a further aspect, the invention provides a method of treating an animal (including a human being) to cure or prevent a fungal infection, which comprises treating said animal with an effective amount of a compound of formula (I), or a pharmaceutically acceptable salt, or a pharmaceutically acceptable solvate of either entity, or a pharmaceutical composition containing any of the foregoing.

The invention also includes any novel intermediates described herein, e.g. the compounds of formula (II).

The syntheses of the compounds of the invention and of the intermediates for use therein are illustrated by the following Examples and Preparations.

$^1$H Nuclear magnetic resonance (NMR) spectra were recorded using either a Nicolet QE-300 or a Bruker AC-300 spectrometer and were in all cases consistent with the proposed structures. Characteristic chemical shifts (δ) are given in parts-per-million downfield from tetramethylsilane using conventional abbreviations for designation of significant peaks: e.g. s, singlet; d, doublet; t, triplet; q, quartet; m, multiplet.

Mass spectra (m/z) were obtained with a Fisons Instruments Trio 1000 spectrometer using thermospray ionisation.

Room temperature means 20–25° C.

EXAMPLE 1

Trans-(2R,3S)- 1-(1,2,4-triazol-1-yl)-2-(2,4-difluororohenyl)-3-{4-[2-(1-methylpyrazol-5-yl) ethenyl]pheny}butan-2-ol A stirred solution of (2R,3S)-1-(1,2,4-triazol-1-yl)-2-(2, 4-difluorophenyl)-3-(4-iodophenyl)butan-2-ol (Preparation 12; 0.5 g, 1.1 mmol), 1-methyl-5-vinylpyrazole (Preparation 17; 0.14 g, 1.3 mmol), triethylamine (0.25 ml, 2 mmol), palladium acetate (130 mg, 0.6 mmol) and tri-o-tolylphosphine (340 mg, 1.2 mmol) in acetonitrile (25 ml) was heated under reflux for 1 hour and then evaporated under reduced pressure. The residue was partitioned between ethyl acetate (100 ml) and saturated aqueous sodium bicarbonate solution (50 ml), then the organic phase separated, washed with saturated brine (30 ml), dried ($Na_2SO_4$) and evaporated under reduced pressure. The crude product was purified by column chromatography on silica gel, using an elution gradient of hexane:propan-2-ol (90:10 to 75:25), to give the title compound (0.31 g) as a white solid, m.p. 81–83° C., after crystallisation from aqueous ethanol. $[\alpha]_D^{25}$ –55° (c=0.1, $CH_3OH$). $\delta(CDCl_3)$: 1.10(3H, d), 3.30(1H,q), 3.90 and 4.80(2H, AB system), 3.95(3H,s), 4.75(1H,s), 6.45(1H,d), 6.80(2H,m), 7.00(2H, AB system), 7.50(6H,m), 7.70(2H,m). Found: C,64.77; H,5.19; N,15.65. $C_{24}H_{23}F_2N_5O$; 0.50 $H_2O$ requires C,64.85; H,5.44; N,15.76%. m/z 436 (M+1)$^+$.

EXAMPLE 2

Trans-(2R,3S/2S,3R)-1-(1,2,4-triazol-1-yl)-2-(2,4-difluorophenyl)-3-{5-[2-(4-fluorophenyl)ethenyl]pyrid-2-yl}butan-2-ol A stirred solution of (2R,3S/2S,3R)-1-(1,2,4-triazol-1-yl)-2-(2,4-difluorophenyl)-3-(5-bromopyrid-2-yl)butan-2-ol (Preparation 3; 0.5 g, 1.22 mmol), 4-fluorostyrene (0.28 ml, 2.4 mmol), triethylamine (0.28 ml, 2 mmol), palladium acetate (15 mg, 0.07 mmol) and tri-o-tolylphosphine (40 mg, 0.14 mmol) in acetonitrile (20 ml) was heated under reflux for 16 hours and then evaporated under reduced pressure. The residue was partitioned between dichloromethane (50 ml) and saturated aqueous sodium carbonate solution (50 ml), then the organic phase separated, dried ($MgSO_4$) and evaporated under reduced pressure. The crude product was crystallised from ether to provide the title compound (145 mg), m.p. 157–158° C. Found: C,66.24; H,4.87; N,12.20. $C_{25}H_{21}F_3N_4O$ requires C,66.66; H,4.70; N,12.44%.

EXAMPLE 3

Trans-(2R,3S/2S,3R)-1-(1,2,4-triazol-1-yl)-2-(2,4-difluorophenyl)-3-[4-(2-methylsulphonylethenyl)phenyl]butan-2-ol Obtained from (2R,3S/2S,3R)-1-(1,2,4-triazol-1-yl)-2-(2,4-difluorophenyl)-3-(4-iodophenyl)butan-2-ol (Preparation 11) and methyl vinyl sulphone by a procedure similar to that described in Example 2. M.p. 169–171° C. Found: C,58.70; H,5.00; N,9.29. $C_{21}H_{21}F_2N_3O_3S$; 0.25 $(C_2H_5)_2O$ requires C,58.46; H,5.24; N,9.30%.

EXAMPLE 4

Trans-(2R,3S/2S,3R)-1-(1,2,4-triazol-1-yl)-2-(2,4-difluorophenyl)-3-[4-(2-carbamoylethenyl)phenyl]butan-2-ol Obtained from the title compound of Preparation 11 and acrylamide by a procedure similar to that described in Example 2. M.p. 122–124° C. Found: C,61.82; H,5.55; N,12.53. $C_{21}H_{20}F_2N_4O_2$; 0.50 $H_2O$; 0.33 $CH_3CO_2H_5$ requires C,61.42; H,5.46; N,12.84%.

EXAMPLE 5

Trans-(2R,3S/2S,3R)-1-(1,2,4-triazol-1-yl)-2-(2,4-difluorophenyl)-3-{4-[2-(imidazol-1-yl)ethenyl]phenyl}butan-2-ol Obtained from the title compound of Preparation 11 and 1-vinylimidazole by procedure similar to that described in Example 2. M.p. 225–227° C. Found: C,65.34; H,5.24; N,16.39. $C_{23}H_{21}F_2N_5O$ requires C,65.55; H,5.02; N,16.62%.

EXAMPLE 6

Trans-(2R,3S/2S,3R)-1-(1,2,4-triazol-1-yl)-2-(2,4-difluorophenyl)-3-{5-[2-(pyrid-2-yl)ethenyl]pyrid-2-yl}butan-2-ol Obtained from the title compound of Preparation 3 and 2-vinylpyridine by a procedure similar to that described in Example 2. M.p. 139–141° C. Found: C,66.51; H,4.94; N,15.98. $C_{24}H_{21}F_2N_5O$ requires C,66.50; H,4.88; N,16.16%

EXAMPLE 7

Trans-(2R,3S/2S,3R)-1-(1,2,4-triazol-1-yl)-2-(2,4-difluorophenyl)-3-[5-(2-carbamoylethenyl)pyrid-2-yl]butan-2-ol Obtained from the title compound of Preparation 3 and acrylamide by a procedure similar to that described in Example 2. M.p. 170–172° C. Found: C,59.74; H,4.63; N,17.91. $C_{20}H_{19}F_2N_5O_2$ requires C,60.14; H,4.79; N,17.54%.

EXAMPLE 8

Trans-(2R,3S/2S,3R)-1-(1,2,4-triazol-1-yl)-2-(2,4-difluorophenyl)-3-{5-[2-(1-ethoxymethyl-1,2,3-triazol-5-yl)ethenyl]pyrid-2-yl}butan-2-ol Obtained from the title compound of Preparation 3 and 1-ethoxymethyl-5-vinyl-1,2,3-triazole (Preparation 15) by a procedure similar to that described in Example 2 except that 0.3 mol. equiv. of palladium acetate was used and also, instead of tri-o-tolylphosphine, 1,1'-bis(diphenylphosphino)ferrocene (0.3 mol. equiv.). M.p. 161–163° C. Found: C,59.73; H,5.31; N,19.77. $C_{24}H_{25}F_2N_7O_2$; 0.10 $CH_3CO_2C_2H_5$ requires C,59.77; H,5.30; N,20.00%.

EXAMPLE 9

Trans-(2R,3S/2S,3R)-1-(1,2,4-triazol-1-yl)-2-(2,4-difluorophenyl)-3-[5-(3-hydroxy-3-methylbut-1-en-1-yl)pyrid-2-yl]butan-2-ol Obtained from the title compound of Preparation 3 and 2-methylbut-3-en-2-ol by a procedure similar to that described in Example 2. M.p. 159–161° C. Found: C,63.67; H,6.22; N,13.16. $C_{22}H_{24}F_2N_4O_2$ requires C,63.76; H,5.84; N,13.52%.

EXAMPLE 10

Trans-(2R,3S/2S,3R)-1-(1,2,4-triazol-1-yl)-2-(2,4-difluorophenyl)-3-{5-[2-(1,2,3-triazol-4-yl)ethenyl]pyrid-2-yl}butan-2-ol A stirred solution of (2R,3S/2S,3R)-1-(1,2,4-triazol-1-yl)-2-(2,4-difluorophenyl)-3-{5-[2-(1-ethoxymethyl-1,2,3-triazol-5-yl)ethenyl]pyrid-2-yl}butan-2-ol (Example 8; 0.1 g, 0.21 mmol) in a mixture of hydrochloric acid (2M; 2 ml), water (2 ml) and ethanol (4 ml) was heated under reflux for 30 minutes. The bulk of the ethanol was evaporated under reduced pressure, the concentrated reaction solution basified with saturated aqueous sodium carbonate solution and extracted with dichloromethane (4×30 ml), then the combined extracts dried ($Na_2SO_4$) and evaporated under reduced pressure to furnish a brown oil. Trituration of the oil with ether gave an off-white solid which, on crystallisation from hexane:ethyl acetate, afforded the title compound (30 mg), m.p. 192–193° C. Found: C,59.44; H,4.54; N,22.93. $C_{21}H_{19}F_2N_7O$ requires C,59.57; H,4.52; N,23.16%.

PREPARATION 1

2-Ethyl-5-bromopyridine

A solution of ethylmagnesium bromide in dry ether (3M; 100 ml, 0.30 mol) was added dropwise to a stirred, ice-cooled solution of anhydrous zinc chloride (40.9 g, 0.30 mol) in dry tetrahydrofuran (500 ml) under nitrogen and the resulting solution stirred for a further 1 hour before the sequential addition of tetrakis (triphenylphosphine) palladium(0) (1.0 g, 0.87 mmol) and a solution of 2,5-dibromopyridine (50 g, 0.21 mol) in dry tetrahydrofuran (200 ml). The resulting yellow suspension was stirred at room temperature for 18 hours, quenched by the addition of water (200 ml) and evaporated under reduced pressure. The residue was partitioned between dichloromethane (500 ml) and a suspension of ethylenediaminetetraacetic acid (200 g) in water (1 l). The organic phase was separated, combined with a dichloromethane extract (500 ml) of the aqueous phase, dried (MgSO$_4$) and evaporated under reduced pressure. Distillation under reduced pressure of the residue gave the title compound (28.8 g) as a colourless oil, b.p. 123–124° C./8 kPa (60 mm Hg). δ(CDCl$_3$): 1.30(3H,t), 2.80(2H,q), 7.10(1H,d), 7.70(1H,dd), 8.60(1H,d).

PREPARATION 2

2-(1-Bromoethyl)-5-bromopyridine

A stirred solution of the title compound of Preparation 1 (1.86 g, 10 mmol) and N-bromosuccinimide (1.78 g, 10 mmol) in 1,2-dichloroethane (20 ml) was heated to reflux, α,α'-azobis(isobutyronitrile) (20 mg) added and the reaction solution stirred under reflux for 2 hours. The resulting, cool suspension was filtered, the filtrate evaporated under reduced pressure and the residue purified by column chromatography on silica gel, using hexane:dichloromethane (1:1) as eluant, to provide the title compound (2.12 g) as a pale yellow oil. δ(CDCl$_3$): 2.05(3H,d), 5.20(1H,q), 7.35(1H, d), 7.80(1H,d), 8.60(1H,d).

PREPARATION 3

(2R,3S/2S,3R)-1-(1,2,4-Triazol-1-yl)-2-(2,4-difluorophenyl)-3-(5-bromopyrid-2-yl)butan-2-ol A solution of the title compound of Preparation 2 (1.32 g, 5 mmol) and 1-(2,4-difluorophenacyl)-1,2,4-triazole (1.11 g, 5 mmol) in dry tetrahydrofuran (12 ml) was added dropwise to a stirred suspension of zinc powder (0.85 g, 13 mmol) in dry tetrahydrofuran (8 ml) at room temperature under nitrogen. Subsequent addition of iodine (0.25, 1 mmol) caused an exothermic reaction, after which the reaction mixture was quenched by the sequential addition of glacial acetic acid (1 ml) and water (10 ml), then ethyl acetate (30 ml) and ethylenediaminetetraacetic acid disodium salt dihydrate (3.72 g, 10 mmol) were added. The organic phase was separated, dried (MgSO$_4$) and evaporated under reduced pressure, then the residue purified by column chromatography on silica gel using hexane:ethyl acetate (1:1) as eluant, followed by trituration with ether, to furnish the title compound (0.62 g), m.p. 158–161° C. δ(CDCl$_3$): 1.08(3H,d), 4.05 and 4.78(2H,AB system). Found: C,49.81; H,3.55; N,13.45. C$_{17}$H$_{15}$BrF$_2$N$_4$O requires C,49.90; H,3.69; N,13.69%.

Further elution of the above column using hexane:ethyl acetate (1:2) afforded the undesired, minor (2R,3R/2S,3S) diastereoisomeric pair of enantiomers as an oil (0.22 g), which crystallised (m.p. 82–83° C.) on standing at room temperature. δ(CDCl$_3$): 1.50(3H,d), 4.66 and 4.80(2H, AB system). Found: C,49.96; H,3.54; N,13.70. C$_{17}$H$_{15}$BrF$_2$N$_4$O requires C,49.90; H,3.69; N,13.69%.

PREPARATION 4

N,O-Dimethyl-4-iodobenzenehydroxamic acid

A solution of pyridine (104 g, 1.32 mol) in dichloromethane (150 ml) was added dropwise to an ice-cooled, stirred suspension of 4-iodobenzoyl chloride (251 g, 0.94 mol) and N,O-dimethylhydroxylamine hydrochloride (97 g, 0.94 mol) in dichloromethane (850 ml). The mixture was allowed to warm to room temperature and then stirred for a further 18 hours. The resulting solution was evaporated under reduced pressure, the residue dissolved in ethyl acetate (1 l) and this solution then washed sequentially with hydrochloric acid (2M, 3×400 ml) and saturated aqueous sodium bicarbonate solution (300 ml), dried (Na$_2$SO$_4$) and evaporated under reduced pressure. The residue was purified by distillation under reduced pressure to give the title compound (241 g) as a yellow oil, b.p. 130° C./13,3 Pa (0.1 mm Hg). δ(CDCl$_3$): 3.32(3H,s), 3.50(3H,s), 7.40(2H,d) 7.72 (2H,d).

PREPARATION 5

1-(4-Iodophenyl)-2-(2,4-difluororhenyl)ethanone 2,4-Difluorobenzyl bromide (23.7 ml, 0.114 mol) was added dropwise to a stirred mixture of magnesium turnings (8.1 g, 0.183 mol) in dry ether (300 ml) under nitrogen. The mixture was warmed initially until initiation of the reaction occurred and, thereafter, said bromide was added at such a rate as to maintain gentle reflux. After 1 hour, the resulting solution of the Grignard reagent was added dropwise to a solution of the title compound of Preparation 4 (45.71 g, 0.157 mol) in dry ether (300 ml) at about –70° C. and the mixture allowed to warm to room temperature overnight (18 hours). The resulting mixture was partitioned between saturated aqueous ammonium chloride solution and ethyl acetate, then the organic phase separated, dried (MgSO$_4$) and evaporated under reduced pressure, to provide the title compound (38.71 g) as a white solid. δ(CDCl3): 4.23(2H,s), 6.83(2H,m), 7.17(1H,dt,J=7.0 and 8.5 Hz), 7.72(2H,d,J=9.0 Hz), 7.84(2H,d,J=9.0 Hz).

PREPARATION 6

1-(4-Iodophenyl)-2-(2,4-difluorophenyl)Prop-2-enone

Bis(dimethylamino)methane (8.78 ml, 0.075 mol) was added dropwise to a stirred suspension of the title compound of Preparation 5 (17.73 g, 0.0495 mol) in acetic anhydride (23.1 ml, 0.248 mol) at room temperature. There was an exothermic reaction, the temperature of the mixture rising to about 60° C. After the end of the addition the mixture was stirred at room temperature for 35 minutes, then ice-water added to hydrolyse the excess acetic anhydride. After a further 30 minutes, the organic material was extracted into ethyl acetate and the combined extracts washed sequentially with dilute hydrochloric acid and saturated aqueous sodium bicarbonate solution, dried (MgSO$_4$) and evaporated under reduced pressure to furnish the title compound (17.03 g) as a white solid. δ(CDCl$_3$): 5.90(1H,s), 6.14(1H,s), 6.84(1H, ddd,J=2,8 and 12 Hz), 6.95(1H,dt,J=2 and 8 Hz), 7.39(1H, dt,J=7 and 9 Hz), 7.59(2H,d,J=9 Hz), 7.83(2H,d,J=9 Hz).

PREPARATION 7

(2R,2S)-2-(2,4-Difluorophenyl)-2-(4-iodobenzoyl) oxirane

Benzyltrimethylammonium hydroxide (40% aqueous solution; 3.44 ml, 8.2 mmol) was added in one portion to a solution of the title compound of Preparation 6 (37.3 g, 100.8 mmol) and t-butylhydroperoxide (3M in trimethylpentane; 36.6 ml, 109 mmol) in toluene (550 ml) at room temperature. After 2 hours, the mixture was washed with water (2×500 ml), dried (MgSO$_4$) and evaporated under reduced pressure to afford the title compound (37.46 g) as a white solid. δ(CDCl$_3$): 3.22(1H,d,J=5 Hz), 3.42(1H,d,J=5 Hz), 6.80(1H,ddd,J=2,8 and 12 Hz), 6.93(1H,dt,J=2 and 8 Hz), 7.47(1H,dt,J=7 and 9 Hz), 7.70(2H,d,J=9 Hz), 7.77(2H, d, J=9 Hz).

PREPARATION 8

(2R,2S)-2-(2,4-Difluororhenyl)-2-[1-(4-iodophenyl) ethenyl]oxirane n-Butyllithium (2.5M in hexane; 50 ml, 125 mmol) was added dropwise over 10 minutes to a stirred suspension of methyltriphenylphosphonium bromide (45.0 g, 126 mmol) in dry tetrahydrofuran (600 ml) at about −70° C. under nitrogen. The mixture was allowed to warm to −20° C. over 20 minutes, then a solution of the title compound of Preparation 7 (37.46 g, 97 mmol) in dry tetrahydrofuran (200 ml) was added over 5 minutes. This mixture was allowed to warm to room temperature, stirred for a further 84 hours, treated with 10% aqueous ammonium chloride solution (500 ml) and concentrated under reduced pressure. The organic material was extracted into ethyl acetate and the combined extracts dried (MgSO$_4$) and evaporated under reduced pressure. The resulting solid residue was treated with boiling hexane (3×500 ml) and the remaining solid discarded. The combined hexane solutions were filtered through a short pad of silica gel and evaporated under reduced pressure to give the title compound (34.3 g) as a yellow oil. δ(CDCl$_3$): 3.13(1H,d,J=5 Hz), 3.17(1H,d,J=5 Hz), 5.45(2H,m), 6.72 (1H,m), 6.80(1H,m), 7.14(2H,d,J=9 Hz), 7.39(1H,dt,J=7 and 9 Hz), 7.60(2H,d, J=9 Hz).

PREPARATION 9

(2R,2S)-1-(1,2,4-Triazol-1-yl)-2-(2,4-difluorophenyl)-3-(4-iodophenyl)but-3-en-2-ol Sodium 1,2,4-triazole (12.15 g, 133 mmol) was added to a solution of the title compound of Preparation 8 (34.3 g, 89 mmol) in dry dimethylformamide (350 ml) at about 70° C. under nitrogen. The resulting mixture was stirred for 5 hours, then allowed to cool and the solvent removed by evaporation under reduced pressure. The residue was dissolved in ether (800 ml) and the solution washed with water (2×500 ml), dried (MgSO$_4$) and treated with silica gel (60–200μ; 75 g). The ether was evaporated under reduced pressure and the residual solid applied to a silica gel column (40–60μ; 300 g). Elution with a solvent gradient of hexane-:ethyl acetate (100:0 to 25:75), followed by evaporation under reduced pressure of the required eluate fractions, provided the title compound (23.8 g) as a white foam. δ(CDCl$_3$): 4.55(1H,d,J=15 Hz), 4.90(1H,d,J=15 Hz), 5.16 (1H,s), 5.25(2H,s), 6.70(2H,m), 7.03(2H,d,J=9 Hz), 7.43 (1H,dt,J=7 and 9 Hz), 7.58(2H,d,J=9 Hz), 7.79(1H,s), 7.80 (1H,s).

PREPARATION 10

(2R)- and (2S)-1-(1,2,4-Triazol-1-yl)-2-(2,4-difluorophenyl)-3-(4-iodophenyl)but-3-en-2-ol The title compound of Preparation 9 was resolved by chiral HPLC using a "Chiralpak AD" (Trade Mark) column and hexane:ethanol (95:5) as eluant. Fractions containing each enantiomer were combined and evaporated under reduced pressure, then the residues further purified by column chromatography on silica gel, using dichloromethane:methanol (95:5) as eluant, followed by trituration with ether.

Analytical HPLC indicated>99% ee for each enantiomer:

for (A), the required (2R)-enantiomer (peak 2), m.p. 111–112° C. and [α]$_D^{25}$ −49° (c=0.1, CH$_3$OH). Found: C,47.52; H,2.97; N,9.09. C$_{18}$H$_{14}$F$_2$IN$_3$O requires C,47.70; H,3.11; N,9.27%.

for (B), the (2S)-enantiomer (peak 1), m.p. 110–111° C. and [α]$_D^{25}$ +41° (c=0.1, CH$_3$OH). Found: C,47.88; H,3.02; N,9.29. C$_{18}$H$_{14}$F$_2$IN$_3$O requires C,47.70; H,3.11; N,9.27%.

PREPARATION 11

(2R,3S/2S,3R)-1-(1,2,4-Triazol-1-yl)-2-(2,4-difluorophenyl)-3-(4-iodophenyl)butan-2-ol A stirred solution of the title compound of Preparation 9 (1.0 g, 2.2 mmol) and p-toluenesulphonylhydrazide (4.1 g, 22 mmol) in toluene (30 ml) was heated under reflux for 3 hours, allowed to cool to room temperature, diluted with ethyl acetate (30 ml) and washed with aqueous sodium hydroxide solution (2M; 2×30 ml). The combined aqueous washings were washed with ethyl acetate, then the combined organic solutions washed with saturated brine (30 ml), dried (MgSO$_4$) and evaporated under reduced pressure. The residue was purified by column chromatography on silica gel, using an elution gradient of hexane:ethyl acetate (3:1 to 1:3), whereupon the first diastereoisomeric pair of enantiomers to elute was the title compound (0.30 g), obtained as a white solid, m.p. 169–171°, after trituration with hexane containing a trace of ethyl acetate. δ(CDCl$_3$): 1.10(3H,d), 3.30(1H, q), 3.80 and 4.80(2H,AB system), 4.90(1H,s), 6.80(2H,m), 7.30(2H,m), 7.45(1H,m), 7.70(4H,m). Found: C,47.66; H,3.55; N,9.19. C$_{22}$H$_{25}$F$_3$ClN$_5$O$_3$ requires C,47.49; H,3.54; N,9.23%.

PREPARATION 12

(2R,3S)-1-(1,2,4-Triazol-1-yl)-2-(2,4-difluorophenyl)-3-(4-iodophenyl)butan-2-ol Obtained from the title compound of Preparation 10A by a procedure similar to that described in Preparation 11 followed by crystallisation from aqueous ethanol, m.p. 104° C. and [α]$_D^{25}$ −44° (c=0.1, CH$_3$OH). Found: C,47.42; H,3.64; N,9.11. C$_{22}$H$_{25}$F$_3$ClN$_5$O$_3$ requires C,47.49; H,3.54; N,9.23%. m/z 456(M+1)$^+$.

PREPARATION 13

1-Ethoxymethyl-1,2,3-triazole

Chloromethyl ethyl ether (125 g, 1.32 mole) was added dropwise over 1.5 hours to an ice-cooled, stirred suspension of 1,2,3-triazole (91.4 g, 1.32 mole) and anhydrous potassium carbonate (183 g, 1.32 mole) in acetone (1.5 l). The mixture was then allowed to warm to room temperature and stirred for a further 18 hours. The solvent was evaporated under reduced pressure, the residue dissolved in water (1 l) and the aqueous solution extracted with dichloromethane (3×300 ml). The combined extracts were washed with saturated brine (3×300 ml), dried (Na$_2$SO$_4$) and evaporated under reduced pressure to furnish a pale yellow oil.

Distillation under reduced pressure of the oil initially afforded 2-ethoxymethyl-1,2,3-triazole (57 g), b.p.<90° C./0.4 kPa (3 mm Hg). δ(CDCl$_3$): 1.17(3H,t), 3.60(2H,q), 5.70(2H,s), 7.70(2H,s). Found: C,47.36; H,7.23; N,32.62. $C_5H_9N_3O$ requires C,47.19; H,7.14; N,33.05%.

Continued distillation yielded the title compound (73 g), b.p. 92–93° C./0.4 kPa (3 mm Hg). δ($CDCl_3$): 1.15(3H,t), 3.56(2H,q), 5.70(2H,s), 7.77(1H,s), 7.79(1H,s). Found: C,46.30; H,7.52; N,33.29. $C_5H_9N_3O$ requires C,47.19; H,7.14; N,33.05%.

PREPARATION 14

1-Ethoxymethyl-5-formyl-1,2,3-triazole n-Butyllithium (2.5M in hexane; 11.3 ml, 28.3 mmol) was added dropwise to a stirred solution of the title compound of Preparation 13 (3.0 g, 23.6 mmol) in dry tetrahydrofuran (100 ml) at about −70° C. under nitrogen. The white suspension was stirred for a further 30 minutes, then a solution of dry dimethylformamide (3.66 ml, 47.2 mmol) in dry tetrahydrofuran (3 ml) was added dropwise. The resulting solution was allowed to warm to room temperature, stirred for a further 30 minutes and treated with saturated aqueous ammonium chloride solution (20 ml) and water (30 ml). The organic phase was separated, combined with dichloromethane extracts (2×50 ml) of the aqueous phase, dried ($Na_2SO_4$) and evaporated under reduced pressure. The crude product was purified by column chromatography on silica gel, using an elution gradient of hexane:ethyl acetate (3:1 to 2:1), to afford the title compound (1.0 g) as a colourless oil. δ($CDCl_3$): 1.15(3H,t), 3.60(2H,q), 6.00(2H, s), 8.25(1H,s), 10.10(1H,s). m/z 156 $(M+1)^+$.

PREPARATION 15

1-Ethoxymethyl-5-vinyl-1,2,3-triazole

Obtained from the title compound of Preparation 14, by a procedure similar to that described in Preparation 8, as a colourless oil. δ($CDCl_3$): 1.15(3H,t), 3.50(2H,q), 5.55(1H, d), 5.70(2H,s), 5.90(1H,d), 6.70(1H,dd), 7.80(1H,s).

PREPARATION 16

1-Methyl-5-formylpyrazole

Obtained from 1-methylpyrazole by a procedure similar to that described in Preparation 14. δ($CDCl_3$): 4.20(3H,s), 6.90(1H,s), 7.55(1H,s), 9.85(1H,s).

PREPARATION 17

1-Methyl-5-vinylpyrazole

Obtained from the title compound of Preparation 16 by a procedure similar to that described in Preparation 8. δ($CDCl_3$): 3.90(3H,s), 5.35(1H,d), 5.70(1H,d), 6.40(1H,d), 6.60(1H,dd), 7.40(1H,d).

Biological Activity

The Table below illustrates the in vivo activity against acute systemic candidosis in immune-normal mice for a selection of the compounds of the invention.

Mice were infected intravenously with *Candida albicans* in order to establish a systemic infection (all untreated control mice died by 2 days post-infection). Compound efficacy was assessed on the basis of survival after oral dosing (0.1–5 mg/kg; 1, 4 and 24 hours post-infection) and was measured as the dose protecting 50% of mice on day 2 post-infection.

TABLE

| EXAMPLE | $PD_{50}$ (mg/kg) |
|---|---|
| 1 | <0.10 |
| 5 | 0.18 |
| 9 | 0.18 |
| 10 | 0.32 |

Safety Profile

The compounds of the invention have not been found to exhibit any overt signs of toxicity. For example, in a 7-day toxicity study in rats (30 mg/kg p.o., o.d.), Example 1 elicited no adverse effects.

We claim:

1. A compound of formula (I)

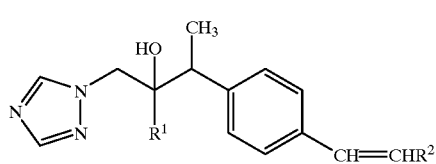

or a pharmaceutically acceptable salt thereof, $R^1$ is phenyl substituted with 1 to 3 substituents each independently selected from halo and $CF_3$;

$R^2$ is (hydroxy)$C_1$–$C_4$ alkyl, $CONH_2$, $S(O)_m$($C_1$–$C_4$ alkyl), Ar or Het;

m is 1 or 2;

Ar is phenyl optionally monosubstituted with halo or $CF_3$;

and Het is selected from the group consisting of pyrazolyl, wherein the foregoing Het group is optionally substituted with $C_1$–$C_4$ alkyl or ($C_1$–$C_4$ alkoxy)methyl.

2. A compound according to claim 1 wherein $R^1$ is phenyl substituted by 1 or 2 substituents each independently selected from F and Cl; $R^2$ is hydroxypropyl, $CONH_2$, $SO_2CH_3$, Ar or Het; Ar is fluorophenyl; and Het is a pyrazolyl, wherein said pyrazolyl group is substituted with methyl.

3. A compound according to claim 2 wherein $R^1$ is 2,4-difluorophenyl; and $R^2$ is $C(CH_3)_2OH$, $CONH_2$, $SO_2CH_3$, 4-fluorophenyl, 1-methylpyrazol-5-yl,.

4. A compound according to of claim 1 which is the (2R,3S)-enantiomer of formula (1A):

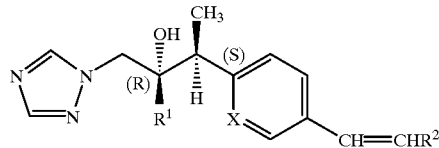

5. A compound according to of claim 1 which is the trans-alkene isomer.

6. A compound according to claim 5 which is selected from trans-(2R,3S)-1-(1,2,4-triazol-1-yl)-2-(2,4-difluorophenyl)-3-{4-[2-(1-methylpyrazol-5-yl) ethenyl]phenyl}butan-2-ol;

or a pharmaceutically acceptable salt thereof.

7. A pharmaceutical composition comprising a compound of claim 1, together with a pharmaceutically acceptable diluent or carrier.

* * * * *